United States Patent [19]

DiSapio et al.

[11] Patent Number: 4,874,129
[45] Date of Patent: Oct. 17, 1989

[54] MULTI-LAMINATE FRAGRANCE RELEASE DEVICE

[75] Inventors: Alfred J. DiSapio, Greenwich, Conn.; William R. Pfister, Bay City; Mary A. Sheeran, Midland, both of Mich.

[73] Assignee: Dow Corning Corporation, Midland, Mich.

[21] Appl. No.: 213,738

[22] Filed: Jun. 30, 1988

[51] Int. Cl.⁴ .................................................. A61L 9/12
[52] U.S. Cl. ............................................ 239/36; 239/53
[58] Field of Search ......................... 239/34, 36, 53–56; 428/905

[56] References Cited

U.S. PATENT DOCUMENTS

| | | | |
|---|---|---|---|
| 2,545,160 | 3/1951 | Miller | 239/55 X |
| 3,412,907 | 11/1968 | Faso | 428/905 X |
| 3,494,505 | 2/1970 | Huebner et al. | 428/905 X |
| 3,955,706 | 5/1976 | Whitaker | 239/55 X |
| 4,283,011 | 8/1981 | Spector | 239/36 |
| 4,720,409 | 1/1988 | Spector | 428/905 X |
| 4,744,514 | 5/1988 | Gadowa | 239/36 |

Primary Examiner—Andres Kashnikow
Assistant Examiner—Kevin P. Weldon
Attorney, Agent, or Firm—Jim DeCesare

[57] ABSTRACT

A multi-layered multi-laminate sustained release device capable of releasing fragrances, colognes, and perfumes, at a controlled rate for a prolonged period of time and having a first layer of a pressure sensitive adhesive release liner for providing a protective peel strip for the device, a second layer of a silicone pressure sensitive adhesive for adhering the device to a substrate to which it is applied including human skin, a third layer of a fragrance oil impregnated matrix of a silicone material selected from the group consisting of silicone elastomers, silicone elastomers having adhesive characteristics, and elastomeric silicone pressure sensitive adhesives, and a fourth layer of a permeable facestock backing member on the surface of the device for controlling the rate of release of the fragrance oil from the impregnated matrix.

22 Claims, 2 Drawing Sheets

MULTI-LAMINATE FRAGRANCE RELEASE DEVICE

BACKGROUND OF THE INVENTION

This invention relates to a fragrance controlled release device constructed from a silicone elastomer and/or a silicone pressure sensitive adhesive. The devices may be attached to household and industrial substrates in one embodiment, and in another embodiment may include colognes and perfumes where the device is intended to be adhered to human skin as a substrate for releasing fragrances, colognes, and perfumes into the environment about the skin rather than into the skin.

Odor modification is the intentional change of one odor by the addition of another more acceptable odor. Air fresheners, perfumes, and industrial deodorants typify odor modifiers, in that they employ fragrance materials for odor control by altering a malodor to a more pleasant character or to an acceptable level. Among the most serious effects of malodors are coughing, headache, nausea, irritation of mucous membranes, and shortness of breath. The need for control of such effects is obvious in locations such as nursing homes, hospitals, restaurants, houses, automobiles, boats, and in the work-a-day environment. Malodors that must be combatted are human body odor, cigarette smoke, toilet odors, and the odor of cooking foods, for example. Generally, the control of body odor is by means of colognes and perfumes, whereas fragrances containing products are employed for industrial and household applications. The prior art is replete with delivery systems for fragrances, colognes, and perfumes. Exemplary systems for the application of fragrances and air fresheners locally or into the immediate environment are sprays, aerosols, sticks, daps, liquid creams and lotions, atomizers, cellulosic and paper matrices. One method developed for timed or controlled release is by means of matrix devices in which a solute to be delivered is compounded in a matrix, generally a polymer such as cellulose esters, polyvinylchloride, polytetrafluoroethylene, polypropylene, polycarbonate, polyethylene, polystyrene, and nylon, which may be in the form of a flat sheet. The solute agent is then released from the matrix by diffusion, and the rate of release decreases with time and is not constant and is typified by first order release kinetics. A relatively constant release rate, characterized by zero order release kinetics, can be achieved by means of depot or reservoir devices in which the rate controlling membrane encloses a cavity that contains the active solute ingredient. The reservoir provides substantially constant solute activity until the solute is exhausted by diffusion. However, the controlled release devices of the prior art suffer from the disadvantage that the duration of fragrance release is limited, often requiring many daily as well as many weekly applications in order to insure the activity of these products. In contrast, the present invention provides new delivery methods and improved controlled release devices for sustaining the release of fragrances, colognes, and perfumes. In published unexamined European Patent Application No. 0186146A2, dated July 2, 1986, of Japan Liquid Crystal Co., Ltd., it is stated that the direct addition of perfume to a synthetic resin compound is not practical or effective because the perfume is volatile, liable to denature, and unstable to heat, so that it is difficult to mold a mixture of perfume and a synthetic resin into a desired shape. The patentee therefore forms an inclusion compound of a perfume in cyclodextrin, powders and dries the inclusion compound, and mixes the powder with the synthetic resin to form products. While the patentee mentions silicone resin as a synthetic resin, products of silicone resin containing perfume are not disclosed, rather the silicone resin is employed with the inclusion compound of cyclodextrin, liquid paraffin, and benzotriazole, to produce semiconductor substrates exhibiting rust preventative, mold-mildew proofing, or antifungal effects. In accordance with the present invention, however, improved and unexpected results are obtained contrary to such teachings and in the absence of the necessity of pre-forming the perfume into an inclusion composition for later formulation into a resin. In another published unexamined European Patent Application No. 0218891A2 dated April 22, 1987, of Union Camp Corporation, a silicon rubber being a cross-linked silicone elastomer of the type vulcanized at room temperature is used in the construction of an elongated hollow cylindrical body member that includes a chamber containing about fifty grams of a volatile liquid fragrance that is intended to be diffused through the cylinder walls and into the atmosphere. A companion application no. 0218892A2 used the same silicone rubber material but in the shape of a closure member for a glass container holding about fifty grams of volatile liquid fragrance which diffuses into the atmosphere through the silicone elastomer closure member. In the U.S. Pat. No. 4,600,146, dated July 15, 1986, to Shin-Etsu Chemical Col, Ltd., a polymeric material such as an organopolysiloxane is formed into a capillary tube that is wire reinforced and filled with fragrance material which diffuses into the atmosphere through the walls of the tube. While these devices utilize silicone materials for diffusion of fragrances into the atmosphere, the devices are cumbersome to handle and expensive to manufacture, and are complex in design in comparison to the simple multi-laminate patch type of fragrance releasing elements of the present invention. Laminate-type systems are known as in U.S. Pat. No. 4,638,043, issued Jan. 20, 1987, in which heat liable drugs are released from a polyurethane matrix that has been light cured rather than heat cured so as not to inactivate the drug. Such a device differs from the present invention in that it is limited to drugs or therapeutic agents, and as a transdermal delivery system, infuses therapeutic agents into the skin, whereas the devices of this invention release fragrances in the opposite direction. Further, the present invention relies upon heat to cure some matrix materials which would otherwise inactivate a system of the type described in U.S. Pat. No. 4,638,043, and in a specific embodiment, includes an impermeable layer for preventing interaction of the fragrance with the skin, which would render devices of the type in U.S. Pat. No. 4,638,043, inoperative. Except for the inclusion of heat curable matrix materials, the same differences exist between the devices of the present invention and those depicted in U.S. Pat. No. 4,655,767, issued Apr. 7, 1987. Further, in the latter patent an impermeable foil or polymer covers the elastomeric drug releasing body whereas in the device of this invention the outer layer is permeable to the fragrance to be released. In U.S. Pat. Nos. 4,703,070, and 4,725,575, issued Oct. 27, 1987, and Feb. 16, 1988, respectively, silicone rubber matrices are disclosed similar to those employed herein. However, in the former patent a compatabilizing agent is required, and neither teach the particulars of the multi-laminate layers employed herein especially the rate controlling outer layer, and the impermeable inner layer which prevents interaction of fragrance with the skin and has utility for individuals otherwise allergic to a particular fragrance due to irritant reaction or skin sensitivity.

SUMMARY OF THE INVENTION

This invention is directed to a new means of application of fragrances, colognes, and perfumes, for personal use and is an improvement over spray-type and topical methods of application of fragrances, colognes, and perfumes, The devices presented herein include the advantage of possessing the capability of prolonged release without frequent renewal of the fragrance, cologne, and perfume, and the devices are adapted to be adhered to the skin of the user or to the user's clothing or personal items including handbags. Such devices further may be in the form of a circular patch and include designer and decorative effects being, for example, imprinted with various colors or designs, and are capable of being worn and displayed as jewelry by males or females of various age groups including pre-teens, teens, and adults.

The invention is also directed to a silicone device for the controlled sustained release of fragrances, air fresheners, and other volatile materials which have desirable organoleptic characteristics including odor neutralization, for use in industrial and household applications. Among the advantages of the device presented herein are that it is simple in its design, small in size, light-weight, and is decorative, providing it with designer qualities. Such devices present a new mode of applying fragrances and air fresheners for industrial and household use, and are in the form of an adhesive patch which controls the release of fragrances and air fresheners into bathrooms, kitchens, trash cans, clostes, automobiles, boats, suitcases, and shoes, for example.

The invention is further directed to a multi-layered multi-laminate fragrance sustained release device capable of releasing fragrances, colognes, and perfumes, at a controlled rate for a prolonged period of time and having a first layer of a pressure sensitive adhesive release liner for providing a protective peel strip for the device, a second layer of a silicone pressure sensitive adhesive or other suitable pressure sensitive adhesive which affixes the device to a substrate, including human skin, a third layer of a fragrance oil impregnated matrix of a silicone material selected from the group consisting of silicone elastomers or silicone elastomers having adhesive characteristics, and elastomeric silicone pressure sensitive adhesives, and a fourth layer of a permeable facestock backing member on the surface of the device for controlling the rate of release of the fragrance oil from the impregnated matrix.

Preferably, the fragrance oil in the impregnated matrix constitutes about one half of one percent to forty weight percent. The matrix may also include a release rate modifying excipient for increasing the solubility of the fragrance in the matrix resulting in an increase in the release capability of the device. The excipient is a material selected from the group consisting of glycerol, propylene glycol, polyethylene glycol, mineral oil, coconut oil, isopropyl palmitate, and isopropyl myristate. The fragrance oil together with the excipient constitute from about one-half of one percent by weight to about forty percent by weight of the impregnated matrix. The silicone pressure sensitive adhesive release liner can constitute a polyester material, such as supplied by 3M Company (SCOTCHPAK TM 1022) or by Akrosil Company (SILOX TM ). The permeable facestock backing member is constructed of a material selected from the group consisting of wovens, non-wovens, and porous thermoplastics, and includes decorative, ornate, and varied colored, designs on the surface thereof. In a particular embodiment of the device of the present invention, the fragrance oil impregnated matrix constitutes at least three separate and distinct layers, each of the three layers of the fragrance oil impregnated matrix including a fragrance oil differing from the fragrance oil in one of the other of the layers of the matrix. An impermeable backing member can also be included as a separate layer for the purpose of preventing the fragrance oil in the impregnated matrix from interacting with the substrate to which the device is applied. In the ideal embodiment, the silicone material is selected from the group consisting of hydroxy or methoxy end capped silicone pressure sensitive adhesives, platinum addition cured silicone elastomers, tin catalyzed condensation cured silicone elastomers, photoinitiated UV cured silicone elastomers, acetoxy cured silicone elastomers, methoxy cured silicone elastomers, and oxime cured silicone elastomers. In one preferred embodiment, the silicone material is a tin catalyzed condensation cured silicone elastomer hereinafter referred to and shown in the Tables and Examples as RTV (room temperature vulcanizing) and is composed of two components, the first being a hydroxy-endblocked organopolysiloxane containing a reinforcing filler, and the second component being the organo-tin catalyst. This material cures at about twenty degrees centigrade, and is more specifically defined, for example, in European published unexamined Patent Application Nos. 82304903.6, filed Sept. 17, 1982, and published Apr. ≢, 1983, and 82306488.6, filed Dec. 6, 1982, and published June 15, 1983.

The layer of silicone pressure sensitive adhesive used to adhere the device to the substrate as well as the additional layers of the silicone pressure sensitive adhesive that occur in selected embodiments of the device is ideally a pressure sensitive adhesive hereinafter referred to as PSA consisting of a polydiorganosiloxane resin containing hydroxy-functionality, and a high molecular weight polydimethylsiloxane gum, more specifically detailed in U.S. Pat. No. 4,655,767, issued Apr. 7, 1987. Amine compatable PSA's can also be used and are referred to hereinafter as PSA-AC.

It is therefore an object of the present invention to eliminate or substantially reduce the initial and undesirable high concentration burst of conventional fragrance, cologne, and perfume, controlled release devices, which occurs immediately following application of such devices including aerosols.

It is also an object of the present invention to provide for the controlled release of fragrances, colognes, and perfumes, at a constant rate as against time in a reservoir-type device, or at a rate which is proprotional to the square root of time in a matrix-type device.

It is a further object of the present invention to provide for the sustained release of fragrances, colognes, and perfumes, in order to insure effective release of the fragrance, cologne, and perfume, for periods of eight hours in personal use, and upwards of periods of weeks in household and industrial applications.

It is, in addition, an object of the present invention to provide a patch-like device possessing designer-like qualities which is capable of being applied to a substrate including the skin or clothing of the user, and which can be affixed to the skin of the user either above or below the clothes line, and which may be fabricated in various colors, shapes, and designs of decorative characteristics, and being light in weight of the order of about five grams or less.

While the invention will be described hereinafter and in the accompanying Tables and Examples in terms of specific fragrances, colognes, and perfumes, it should be understood that the concepts and features of the invention described herein are not so limited but include any type of fragrance, cologne, or perfume, compatible with the materials, depending upon the category of use of the device of the present invention and including the group of people to whome it is sought to attract. For example, the fragrance may be a natural product such as Ambergris, Benzoin, Civet, Clove Leaf Oil, Galbanum, Jasmine Absolute, Labdanum, Mate', Melilot, Mimosa, Musk Tonquin, Myrrh, Mousse de Chene, Olibanum, Opopanax, Orris, Patchouli, Rosemary Oil, Sandalwood Oil, Vetivert Oil, and Violet Leaves Absolute. Among the various aroma chemicals that may be employed in addition to the foregoing natural products are, for example, acetylated cedarwood terpenes, amylcinnamic aldehyde, amyl salicylate, methyl salicylate, benzyl acetate, benzyl salicylate, p-tert-butylcyclohexyl acetate, citronellol, coumarin, Galaxolide, geraniol, hexylcinnamic aldehyde, isobornyl acetate, linalool, linalyl acetate, Lyral, musk ambrette, phenethyl alcohol, tetrahydromuguol, and terpinyl acetate. Fragrances that have become classics as descriptors for other fragrances in the same family are also included herein and would comprehend the Straight Floral Family, Floral Bouquet Family, Aldehydic Floral Family, Oriental Family, Chypre Family, Woody Family, Green Family, Citrus Family, Fougere Family, Canoe Family, Musk Family, Animal Family, Leather Family, Spice Family, and the Herbal Family.

These and other features, objects, and advantages, will become apparent when taken in conjunction with the following detailed description of the invention including the various figures of the device set forth in the accompanying drawings.

DETAILED DESCRIPTION OF THE INVENTION

Figure 1:
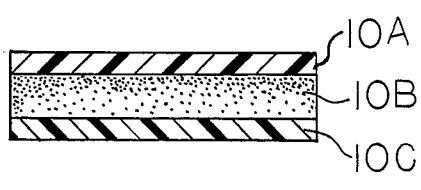
FIGS. 1 and 2 are pictorial representations partly in cross section of embodiments of multilaminate matrix devices of the present invention wherein the devices include the potential capacity of interacting of the fragrance, cologne, and perfume, with the substrate to which they are applied including the skin.

The present invention is related to reservoir and matrix devices which are capable of releasing fragrances, perfumes, and colognes at a controlled rate for a prolonged period of time. The matrix and reservoir devices are illustrated in the various figures in the accompanying drawings and include devices which can be affixed to substrates such as automobiles, boats, toilet bowls, doors, suitcases, shoes, trash cans, handbags, and in closets. The fragrance containing matrix is an elastomer material or an elastomeric pressure sensitive adhesive. The pressure sensitive adhesive is preferably a composition such as PSA or PSA-AC as defined above, or other hydroxy-end capped silicone pressure sensitive adhesive or elastomer having adhesive characteristics of being solvent resistant and curable. The solvent carrier for these pressure sensitive adhesives is freon, xylene, toluene, naphtha, or other organic solvent type. The fragrance containing matrix may also consist of a silicone elastomer. These silicone elastomers can be of the platinum addition cure type, or tin catalyzed condensation cured type including, but not limited to RTV as defined previously, and silicone elastomers of the low temperature vulcanizing type, hereinafter referred to as LTV, obtained from a two-component mixture of organopolysiloxanes formed by an addition cure hydrosilylation reaction facilitated by a platinum catalyst, as detailed, for example, in United Kingdom Patent No. 1412970, filed January 15, 1974, and published Nov. 5, 1975. Such LTV's will cure at temperatures less than or about equal to one hundred degrees centigrade. The silicone elastomers may also be composed of UV cured systems which employ a photoinitiator. The fragrance containing matrix may also consist of a silicone elastomer material that is based on a one-part acetoxy, methoxy, or other alkoxy, or oxime cure system including but not limited to one part RTV elastomers hereinafter referred to as RTV-OP. Silicone adhesives and elastomers are well-suited as matrices due to their high degree of permeation to a wide variety of therapeutic agents, volatile anesthetics as well as gases. The fragrance releasing devices of the present invention are multi-laminate systems which can be fabricated by conventional converting equipment. The fragrance impregnated adhesive, elastomeric adhesive, or elastomeric matrix contains up to about forty weight percent fragrance oil together with various excipients. Active fragrances, perfumes or colognes, may be co-formulated with aqueous or oil type liquid excipients including those excipients which are cosmetically suitable for modifying release rates. Excipients are employed to increase the solubility of active fragrances in the matrix and thereby result in an increase in the release of fragrances from the device. Such excipients may consist of but are not limited to glycerol, propylene glycol, polyethylene glycol, mineral oil, coconut oil, isopropyl palmitate, isopropyl myristate, and various silicone fluids. The permeable backing on the surface of the device includes decorative and ornate materials of various glitters, colors and designs. The permeable backing can be, for example, nonwovens, wovens, and porous thermoplastic materials, as well as silicone materials, which can serve as rate controlling elements of the device. The protective peel strip for silicone pressure sensitive adhesives is preferably of 3M Corporation SCOTCHPAK ™ 1022 polyester release liner or there may be employed a silicone pressure sensitive adhesive release liner supplied by Akrosil Company under the tradename of SILOX ™. Other silicone coated release liners may be used for acrylic or other organic pressure sensitive adhesives. In preparing the devices, an appropriate quantity of fragrance is blended with the silicone adhesive or elastomer base material in a range of preferably between about 0.5 and 40 weight percent depending upon the volatility and desired longevity of the device. Controlled release fragrance devices in accordance with the present invention are manufactured by techniques including but not limited to, for example, injection molding, compression molding, film casting, extrusion, and lamination. The addition cure polymer fragrance systems are cured into elastomer fragrance matrices at 80–100 degrees Centigrade for 2–15 minutes depending upon the matrix thickness. The condensation and UV cure systems are cured into elastomer fragrance matrices at room temperature or cure can be acclerated at higher temperatures. Fragrances which may not be compatible with addition cure systems may be compatible with condensation, UV or alkoxy cure systems, however.

Examples illustrating the concepts of the present invention and demonstrating the compatibility of fragrances with, for example, the composition RTV, which is a room temperature curing tin-catalyzed medium viscosity silicone rubber, hereinafter referred to as RTV, are set forth hereinbelow and the results of these Examples are tabulated and are shown in Table I. In summary, eight dermal fragrance patches of from one to three centimeter diameter were prepared employing RTV as the matrix portion of the device which contained the fragrance oil. These multi-laminate four component devices consist of a permeable facestock material, a silicone elastomer matrix, pressure sensitive adhesive, and a release liner. One particular example of a device shown in FIG. 16 having a multi-layer matrix of three individual and separate matrix layers each containing a different fragrance was also fabricated. Fragrance patches were prepared containing from about 0.5–5 5 weight percent levels of the fragrance oils Citronellal, Gineole, YSL PARIS®, manufactured by Charles of the Ritz Group of New York, New York; JOY®, manufactured by Jean Patou, Inc. of New York, New York; OSCAR de la RENTA®, manufactured by Oscar de la Renta, Ltd. of New York, New York; and IVOIR de BALMAIN ™, manufactured by Balmain International B. V. of Rotterdam, Netherlands. The fragrance patches possessed the characteristic organoleptic properties of each respective fragrance which was noticeable after fabrication and lasted for several weeks. The Examples demonstrate the practicality of incorporating fragrance oil into a silicone elastomeric matrix of RTV to form a fragrance dermal patch having controlled release properties. The fragrance patches were evaluated for cure compatibility and physical characteristics including organoleptic properties. Adhesion of the patch to various substrates was also evaluated. Specifically, formulations of the various perfumes (0.5–5 wt %) were prepared using RTV and catalyzed with 0.5 weight percent of RTV Catalyst. Twenty grams of formulation were then mixed in polypropylene beakers and film-cast between two sheets of Mylar® polyester to form a twenty mil thick matrix. These sheets were oven-cured for one hour at fifty degrees Centigrade and evaluated for physical properties including vulcanization, elasticity, phase separation, surface properties, and scent initially and after periods of twenty-four hours and one week, respectively. Following cure, the polyester was removed from one surface of the matrix which was then transfer-coated with a two mil thick film of PSA-AC. Other formulations were film-cast between Mylar® polyester which releases from the matrix, and kraft paper coated with a silicone paper coating which bonds to the matrix. Following cure of the matrix, the polyester was removed and a two mil thick film of the PSA was transfer-coated to the surface of the matrix. Selected patches were then transfer-coated with a two mil thick film of PSA-AC, and protected with the 3M Corporation SCOTCHPAK® Material 1022 polyester release liner. The samples of the dermal fragrance patches were then die cut into one to three centimeter diameter discs for evaluation. These patches were found to adhere to several substrates including skin, wood, plastic, fiberglass, and metal, and provided prolonged release of fragrance.

The prepared formulations and cured properties of each are detailed in the following Examples I–VIII.

EXAMPLE I 0.5 Wt % Citronellal in RTV Matrix

The essence oil of Citronellal was added at 0.5 weight percent to RTV and a master batch of 18.0 grams was prepared having the following formulation:
0.09 grams Citronellal
17.82 grams RTV
0.09 grams RTV Catalyst The resulting composition was film cast between two sheets of Mylar® and oven cured approximately one hour at fifty degrees Centigrade. When curing was completed, the properties were analyzed with the following results:
Curing ability: easily cured
Elasticity: elastic (very little or no tear)
Phase separation: none
Surface properties: dry
Scent: initial—very clear; after 24 hours —same as initial

EXAMPLE II 0.5 Wt % Cineole in RTV Matrix

The essence oil of Cineole was added at 0.5 weight percent to RTV. A master batch of 18.0 grams was then prepared having the following formulation:
0.09 grams Cineole
17.82 grams RTV
0.09 grams RTV Catalyst This material was film cast between two sheets of Mylar® and oven cured approximately one hour at fifty degrees Centigrade, and when curing was completed, the properties were analyzed with the following results:
Curing ability: easily cured
Elasticity: elastic (very little or no tear)
Phase separation: none
Surface properties: dry
Scent: initial—very clear; after 24 hours —same as initial

EXAMPLE III 0.5 Wt % YSL PARIS ® in RTV Matrix

The essence oil of YSL PARIS ® was added at 0.5 weight percent to RTV. A master batch of 18.0 grams was prepared and having the following formulation:
0.09 grams YSL PARIS ®
17.82 grams RTV
0.09 grams RTV Catalyst This material was film cst between two sheets of Mylar ® and oven cured approximately one hour at fifty degrees Centigrade and when curing was completed, the properties were analyzed and found to be as follows:
Curing ability: easily cured
Elasticity: elastic (very little or no tear)
Phase separation: none
Surface properties: dry
Scent: initial—very clear; after 24 hours —same as initial

EXAMPLE IV 0.5 Wt % IVOIRE de BALMAIN ™ in RTV Matrix

The essence oil of IVOIRE de BALMAIN ™ was added at 0.5 weight percent to RTV and a master batch of 18.0 grams was prepared which had the following formulation:
0.09 grams IVOIRE de BALMAIN ®
17.82 grams RTV
0.09 grams RTV Catalyst This material was film cast between two sheets of Mylar ® and oven cured approximately one hour at fifty degrees Centigrade and when curing was completed, the properties were analyzed and with the following results:
Curing ability: easily cured
Elasticity: elastic (very little or no tear)
Phase separation: none
Surface properties: dry
Scent: initial—very clear; after 24 hours —same as initial

EXAMPLE V 0.5 Wt % JOY ® in RTV Matrix

The essence oil of JOY ® was added at 0.5 weight percent to RTV and a a master batch of 18.0 grams was prepared having the following formulation:
0.09 grams JOY ®
17.82 grams RTV
0.09 grams RTV Catalyst This material was film cast between two sheets of Mylar ® and oven cured approximately one hour at fifty degrees Centigrade and when curing was completed, the properties were analyzed with the following results:
Curing ability: easily cured
Elasticity: elastic (tears very little or not at all)
Phase separation: none
Surface properties: dry
Scent: initial—very clear; after 24 hours —same as initial.

EXAMPLE VI 0.5 Wt % OSCAR de la RENTA ® in RTV Matrix

The essence oil of OSCAR de la RENTA ® was added at 0.5 weight percent to RTV and a master batch of 18.0 grams was prepared having the following formulation:
0.09 grams OSCAR de la RENTA ®
17.82 grams RTV
0.09 grams RTV Catalyst This material was film cast between two sheets of Mylar ® and oven cured approximately one hour at fifty degrees Centigrade and when curing was completed, the properties were analyzed with the following results:
Curing ability: easily cured
Elasticity: elastic (very little or no tear)
Phase separation: none
Surface properties: dry
Scent: initial—very clear; after 24 hours —same as initial

EXAMPLE VII

5% JOY ® in RTV Matrix on Release Paper

The essence oil of JOY ® was added at 5.0 weight percent to RTV and a master batch of 18.0 grams was prepared having the following formulation:
16.24 grams RTV
0.86 grams RTV Catalyst
0.90 grams JOY ®

This material was film cast between Mylar ® and silicone release paper and oven cured approximately one hour at fifty degrees Centigrade and when the curing was completed, the properties were analyzed with the following results:
Curing ability: easily cured
Elasticity: elastic (very little or no tear)
Phase separation: none
Surface properties: dry
Scent: initial—very clear; after 24 hours —same as initial

EXAMPLE VIII 0.5% OSCAR de la RENTA ®, IVOIRE de BALMAIN ®, and YSL PARIS ® Layered on Release Paper The essence oil of OSCAR de la RENTA ®, IVOIRE de BALMAIN ®, and YSL PARIS ® were added at 0.5 weight percent each to RTV and a master batch of 18.0 grams of each were made having the following formulation:
17.82 grams RTV
0.90 grams RTV Catalyst
0.09 grams each of OSCAR de la RENTA ®, IVOIRE de BALMAIN ®, and YSL PARIS ®

Each material was film cast between Mylar ® and silicone release paper in layers of OSCAR de la RENTA ®, IVOIRE de BALMAIN ®, and then YSL PARIS ®, each being oven cured approximately fifteen minutes at eighty degrees Centigrade providing a total curing time of forty-five minutes. When curing was completed, the properties of each of the layers was analyzed with the following results:
Curing ability: easily cured
Elasticity: elastic (very little or no tear)
Phase separation: none
Surface properties: dry
Scent: initial—very clear; after 24 hours —same as initial

TABLE I

| FORMULATIONS OF FRAGRANCE PATCHES | | | |
|---|---|---|---|
| Sample | Polymer | Fragrance | Wt % |
| 1 | RTV | Citronellal | 0.5 |
| 2 | RTV | Cineole (eucalyptol) | 0.5 |

TABLE I-continued

| | | FORMULATIONS OF FRAGRANCE PATCHES | |
|---|---|---|---|
| Sample | Polymer | Fragrance | Wt % |
| 3 | RTV | YSL PARIS ® (Chlon 20th edition) | 0.5 |
| 4 | RTV | IVOIRE de BALMAIN ® (Chlon 28th edition) | 0.5 |
| 5 | RTV | JOY ® (Chlon 5th edition) | 0.5 |
| 6 | RTV | OSCAR de la RENTA ® (Chlon 9th edition) | 0.5 |
| 7 | RTV | JOY ® (Chlon 5th edition) | 5.0 |
| 8* | RTV | OSCAR de la RENTA ® (Chlon 9th edition) | 0.5 |
| | | IVOIRE de BALMAIN TM (Chlon 18th edition) | 0.5 |
| | | YSL PARIS ® (Chlon 20th edition) | 0.5 |

Figure 16:
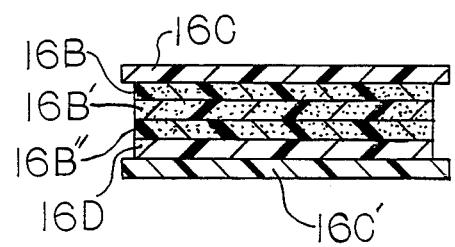
FIG. 16 is a pictorial representation partly in cross-section of another embodiment of the present invention wherein the fragrance containing matrix consists of a plurality of layers each containing a different fragrance.

*This sample was triple layered and is illustrated in FIG. 16.

All of the silicone fragrance formulations cured into elastomeric matrices which liberated fragrance oil, the scent of which could be detected up to five feet away. The cured properties of these formulations are listed in Table II. All of the matrices were elastomeric with high tear strength, and possessed a dry surface with no oiling or phase separation, and liberated scent for up to one week. The release liner was removed easily from selected patches with no transfer of residue. The patches were applied to several substrates as shown below in Table III and adhered in place for up to three weeks. The fragrance oils did not adversely affect the PSA-AC composition at the levels employed. All of the samples were found to possess desirable organoleptic properties.

TABLE II

| | | | CURED PROPERTIES OF FRAGRANCE ELASTOMERS | | |
|---|---|---|---|---|---|
| | | | Phase[c] | Surface[d] | Scent[e] |
| # | Cure[a] | Elasticity[b] | Separation | Properties | 24 hr/ 1 wk |
| 1 | 1 | 1 | no | 3 | 1 1 |
| 2 | 1 | 1 | no | 3 | 1 1 |
| 3 | 1 | 1 | no | 3 | 1 1 |
| 4 | 1 | 1 | no | 3 | 1 1 |
| 5 | 1 | 1 | no | 3 | 1 1 |
| 6 | 1 | 1 | no | 3 | 1 1 |
| 7 | 1 | 1 | no | 3 | 1 1 |
| 8 | 1 | 1 | no | 3 | 1 1 |

[a]cure: 1 = fast cure; 2 = slow cure; 3 = no cure
[b]elasticity: 1 = no tear; 2 = moderate tear; 3 = easy tear
[c]phase separation: yes; no
[d]surface properties: 1 = oily; 2 = slightly oily; 3 = dry
[e]scent: 1 = clear and distinct or same as initial; 2 = slight decrease; 3 = marked decrease

TABLE III

| | Adhesion of Fragrances Dermal Patches | |
|---|---|---|
| # | Substrate | Time[a] |
| 1 | metal | 1 week |
| 5 | vinyl | 2 weeks |
| 5 | wood | 3 weeks |
| 8 | skin | 1 day |
| 5 | skin | 1 day |
| 5 | fiberglass | >3 weeks |

[a]No samples fell from the substrate.

The foregoing data demonstrate that several different types of fragrance oils can be incorporated into a tin catalyzed room temperature condensation cure liquid silicone rubber to form an elastomeric fragrance matrix. The devices can be fabricated by a film cast process between various substrates. A silicone pressure sensitive adhesive is applied to the device to form a multi-laminate system including a permeable backing, RTV fragrance oil matrix, a layer of PSA, and a pressure sensitive adhesive release liner. The devices can be applied to several and varied types of substrates including skin, plastic, fiberglass, wood, and metal. The fragrance release devices of the present invention have utility in many areas including, for example, the household which will provide for the controlled release of fragrances in the form of stick-on air freshener patches. These stick-on air freshener patches can be applied to substrates such as a bathroom toilet bowl, trash cans, kitchen cabinets, closets, refrigerators, inside of shoes, in suitcases, briefcases, pocketbooks, as decorative and accented designer patches for windows, inside decorative flower vases, and in laundry rooms. Another practical application of the patch devices of the present invention is as fragrance releasing devices for automobiles and boats. The patch-type fragrance devices can be applied to substrates such as a dash board, seat back, glove box, ash tray, and in windows, for example. As industrial devices, the patches of the present invention can be applied to substrates in environments such as restrooms, office areas, hallways, and in the various encountered manufacturing areas. The fragrance release devices and patches of the present invention can also take the form of dermal patches which are intended to be applied to the person for personal use. Such devices are intended to be used by the female teen-age population and consist of fragrance patches which are die cut, imprinted and colored with primary colors and fluorescent dyes in the form of various animals, flowers, and cartoon characters which are appealing to a particular age group. For the older female population, the fragrance releasing devices consist of designer patches having decorative qualities such as jewelry. The devices consist of various glitters, silver, and gold, reflective materials configured in ornate patterns with color, and being die cut in various designs. The devices can also consist of more sophisticated designs intended as fresheners for clothing or purses and as adhesive scented name badges.

Figure 2:
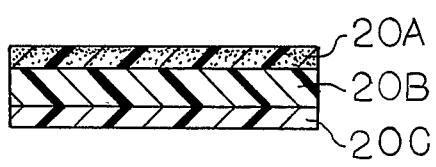

In the drawings, there are depicted four categories, of devices for releasing fragrances, colognes, and perfumes at a controlled and sustained rate. FIGS. 1 and 2, for example, illustrate the matrix type of device and wherein the device possesses the potential of providing interaction of the fragrance with the substrate to which it is applied including human skin. This same general category of device is also set forth in FIGS. 3-7, except that the devices in FIGS. 3-7 are of the reservoir type rather than matrix as FIGS. 1 and 2. In FIGS. 8-10, there is again illustrated the matrix type of device, except that in FIGS. 8-10 the device possesses no potential of providing interaction of the fragrance with the substrate to which it is applied including human skin. This same general category of device is also set forth in FIGS. 11-15, except that the devices in FIGS. 11-15 are of the reservoir type rather than matrix as FIGS. 8-10. The distinguishing feature between the devices of FIGS. 1-7 and the devices of FIGS. 8-15 is that in the devices of FIGS. 8-15 there is included an impermeable backing member which is not present in the devices of FIGS. 1-7. Otherwise, the devices of FIGS. 1-15 are similar structurally, and in view of the similarities, various of the repetitive elements that occur in the several embodiments have been indicated by a combination of numerals and letters, with the letters indicating in general identical types of elements in the several views.

Figure 3:
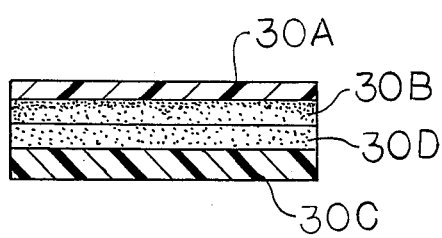
FIGS. 3-7 are pictorial representations partly in cross section of various embodiments of multilaminate reservoir devices of the present invention wherein the devices include the potential capacity of interacting of the fragrance, cologne, and perfume, with the substrate to which they are applied including the skin.
Figure 4:
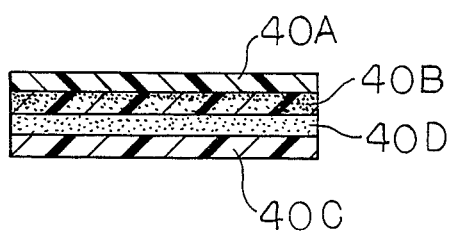
Figure 5:
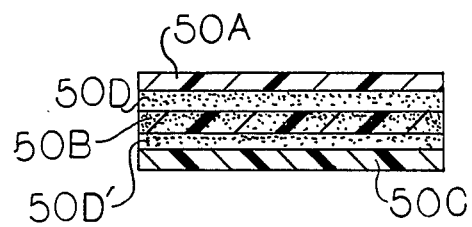
Figure 6:
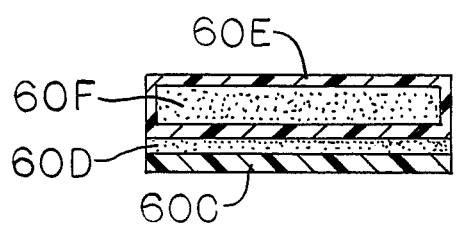
Figure 7:
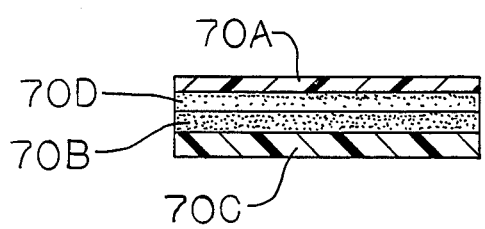
Figure 8:
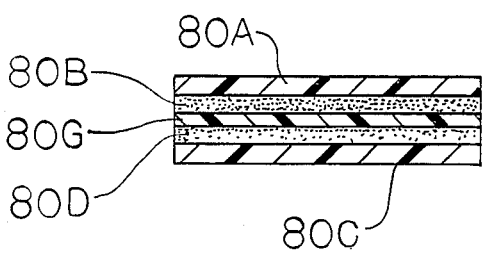
FIGS. 8-10 pictorial representations partly in cross section of embodiments of multilaminate matrix devices of the present invention wherein the devices do not include the potential capacity of interacting of the fragrance, cologne, and perfume, with the substrate to which they are applied including the skin.
Figure 9:
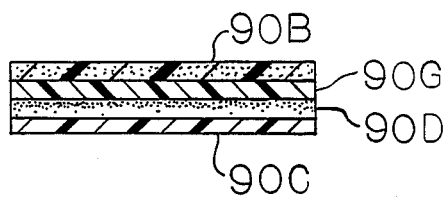
Figure 10:
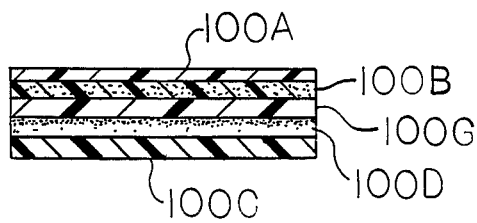
Figure 11:
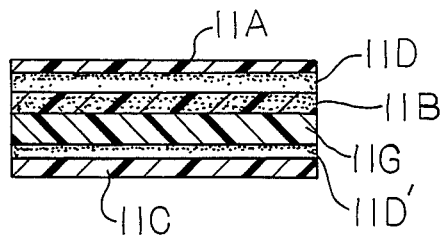
FIGS. 11-15 are pictorial representations parly in cross section of various embodiments of multilaminate reservoir devices of the present invention wherein the devices do not include the potential capacity of interacting of the fragrance, cologne, and perfume, with the substrate to which they are applied including the skin.
Figure 12:
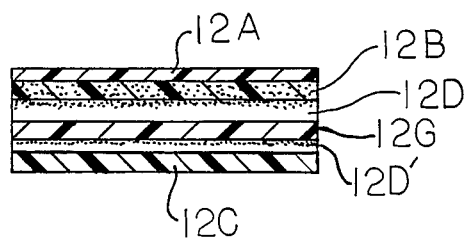
Figure 13:
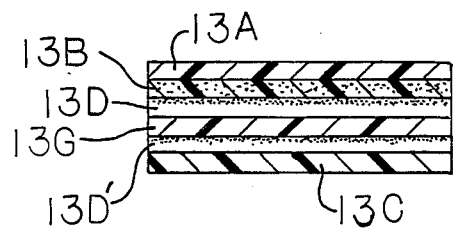
Figure 14:
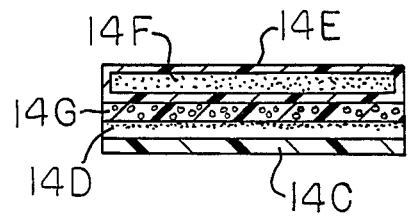
Figure 15:
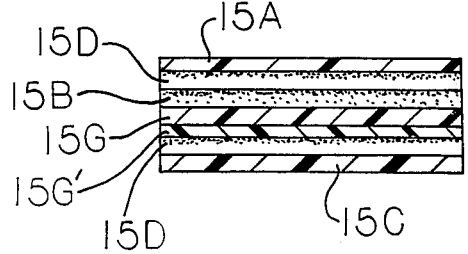

Thus, the permeable backing member 10A in FIG. 1 is 30A in FIG. 3, for example. The fragrance oil impregnated matrix 10B in FIG. 1 is 40B in FIG. 4. In FIG. 1, the pressure sensitive release liner 10C which functions as a protective peel strip is shown again at 50C in FIG. 5. In FIG. 2, the non-fragrance loaded pressure sensitive adhesive layer 20C appears again, for example, in FIG. 6 and is identified at 60D. FIG. 5 includes two non-fragrance loaded pressure sensitive adhesive layers indicated by 50D and 50D' respectively. This also occurs in FIGS. 11–13 and 15. FIG. 13 in fact includes two non-fragrance loaded pressure sensitive adhesive layers identified respectively as 13D and 13D'. The embodiments of FIGS. 6 and 14 each include a rate controlling membrane 60E and 14E respectively, and a fragrance reservoir compartment which can include liquids or solids, indicated respectively at 60F and 14F. The impermeable backing member 80G in FIG. 8 is illustrated also, for example, in FIG. 9 at 90G, and in FIG. 15 there are two impermeable backing members 15G and 15G'. While the fragrance oil impregnated matrix B is shown throughout the figures as a single layer, the matrix B may be of two or three or more separate and distinct layers each containing differing fragrances or mixtures of fragrances as depicted in FIG. 16.

Further and additional test data were generated in the form of Examples and Tables and such data are set forth hereinbelow in order to amplify the concepts of the present invention.

Twenty-three different dermal fragrance patches 1 to 3 cm in diameter were prepared employing LTV and PSA as the matrix portion of the device which contained the fragrance oil. The multi-laminate devices consist of a protective Mylar ® backing material, silicon elastomer matrix, pressure sensitive adhesive and release liner for elastomer systems or a device consisting of a protective Mylar ® backing, permeable kraft paper membrane, fragrance-PSA matrix, and release liner for PSA systems.

Fragrance patches were prepared containing 0.5–5.0 wt % levels of the following oils: Citronellal, Cineole, YSL PARIS ®, JOY ®, OSCAR de la RENTA ®, and IVOIRE de BALMAIN ™. The fragrance patches possessed the characteristic organoleptic properties of each respective fragrance which was noticeable after fabrication and lasted for several weeks. In addition, the systems were functional after storage for 17 months and adhered to metal and wood substrates, and exhibited controlled release of fragrance.

Formulations of various fragrance oils (0.5–5.0 wt %) were prepared using RTV and catalyzed with 0.5 wt % of RTV catalyst immediately prior to use. Twenty grams of formulations were mixed in polypropylene beakers and film-cast between two sheets of Mylar ® polyester to form a 20 mil thick matrix. These formulations were oven-cured for one hour at 50° C. and evaluated for physical properties including vulcanization, cure, elasticity, phase separation, surface properties, and scent, initially, after 24 hours, and one week. Some formulations were compression molded in a hydraulic press at 80° C. for 15 minutes under 12 tons of pressure in a 6"×6"×0.020" mold.

Formulations of various fragrance oils (0.5–5.0 wt %) were prepared using LTV and LTV Curing Agent. These formulations were blended in a ratio of nine parts base to one part curing agent to form a master batch. The appropriate weight of fragrance oil was added and mixed to homogeneity. Matrices were prepared by dispensing the formulation into a 6"×6"×0.20" mold between Milar ® sheets and compression molded at 100° C. for 15 minutes at 12 tons of pressure in a hydraulic press. The matrices can be fabricated by a film casting process as described above.

Formulations of various fragrance oils (0.5 to 5.0 wt %) were prepared using LTV elastomer base and LTV curing agent. These formulations were blended in a ratio of nine parts base to one part curing agent to form a master batch. The appropriate quantity of fragrance oil was added and the matrices were prepared as indicated above.

Formulations of various fragrance oils (0.5–5.0 wt %) were prepared using PSA. This PSA was a 18.5 wt % solution in Freon ® 113. A 50 gram volume of adhesive solution was weighed and mixed with the appropriate wt % of fragrance oil.

The adhesive solution was coated with a Meyer bar (K Bar, No. 8), and drawn down by hand at a relatively constant speed on a release liner held in place on a K-Hand Coater board. The laminate of SCOTCH-PAK ® 1022, fragrance adhesive matrix and Mylar ® was prepared by transfer-coating a sheet of bleached kraft paper over the fragrance adhesive matrix. The coater and the coating bar are products manufactured by Testing Machines Inc. of Amityville, New York.

EXAMPLE IX

The essence of oil of Citronellal was added at 0.5 weight percent to LTV. A master batch of 18.0 grams was prepared by the following formulations:

| Grams | Formulation |
| --- | --- |
| 16.12 | LTV Base |
| 1.79 | LTV Curing Agent |
| 0.09 | Citronellal |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—same as initial after 17 months of storage initial—very clear, some loss of fragrance

EXAMPLE X

The essence of oil of Cineole was added at 1.0 weight percent to LTV. A master batch of 18.0 grams was prepared by the following formulations:

| Grams | Formulation |
| --- | --- |
| 16.04 | LTV Base |
| 1.78 | LTV Curing Agent |
| 0.18 | Cineole |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XI

The essence of oil of IVOIRE de BALMAIN ™ was added at 1.0 weight percent to LTV. A master batch of 18.0 grams was prepared by the following formulations:

| Grams | Formulation |
|-------|-------------|
| 16.04 | LTV Ease |
| 1.78  | LTV Curing Agent |
| 0.18  | IVOIRE de BALMAIN ™ |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XII

The essence of oil of OSCAR de la RENTA ® was added at 5.0 weight percent to LTV. A master batch of 18.0 grams was prepared by the following formulations:

| Grams | Formulation |
|-------|-------------|
| 15.39 | LTV Base |
| 1.71  | LTV Curing Agent |
| 0.90  | OSCAR de la RENTA ® |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XIII

The essence of oil of JOY ® was added at 5.0 weight percent to LTV. A master batch of 18.0 grams was prepared by the following formulations:

| Grams | Formulation |
|-------|-------------|
| 15.39 | LTV Base |
| 1.71  | LTV Curing Agent |
| 0.90  | JOY ® |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XIV

The essence of oil of Citronellal was added at 0.5 weight percent to LTV. A master batch of 18.0 grams was prepared by the following formulations:

| Grams | Formulation |
|-------|-------------|
| 16.12 | LTV Base |
| 1.79  | LTV Curing Agent |
| 0.09  | Citronellal |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Scent: initial—very clear after 24 hours—very clear after 17 months of storage initial—very clear, some loss of fragrance

EXAMPLE XV

The essence of oil of JOY ® was added at 1.0 weight percent to LTV. A master batch of 18.0 grams was prepared by the following formulations:

| Grams | Formulation |
|-------|-------------|
| 16.04 | LTV Base |
| 1.78  | LTV Curing Agent |
| 0.18  | JOY ® |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry Scent: initial—very clear after 24 hours—very clear after 17 months of storage initial—very clear, some loss of fragrance

EXAMPLE XVI

The essence of oil of Cineole was added at 0.5 weight percent to LTV. A master batch of 18.0 grams was prepared by the following formulations:

| Grams | Formulation |
|---|---|
| 16.10 | LTV Base |
| 1.79 | LTV Curing Agent |
| 0.09 | Cineole |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XVII

The essence of oil of YSL PARIS ® was added at 1.0 weight percent to LTV. A master batch of 18.0 grams was prepared by the following formulations:

| Grams | Formulation |
|---|---|
| 16.04 | LTV Base |
| 1.78 | LTV Curing Agent |
| 0.18 | YSL PARIS ® |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XVIII

The essence of oil of Cineole was added at 0.5 weight percent to LTV. A master batch of 18.0 grams was prepared by the following formulations:

| Grams | Formulation |
|---|---|
| 16.12 | LTV Base |
| 1.79 | LTV Curing Agent |
| 0.09 | Cineole |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: cures completely
Elasticity: elastic (very little or no tear)
Phase separation: none
Surface properties: dry
Scent: initial—very clear after 24 hours—very clear after 17 months of storage initial—very clear, some loss of fragrance

EXAMPLE XIX

The essence of oil of Cineole was added at 0.5 weight percent to PSA. A master batch was prepared by the following formulations:

| Grams | Formulation |
|---|---|
| 50.00 | PSA |
| 0.045 | Cineole |

This batch was hand-coated with a Meyer rod onto SCOTCHPAK ® 1022 release liner, allowed to dry, and transfer-coated onto white kraft paper.

Following fabrication, the properties were evaluated with the following results:
Adhesion: good adhesive properties
Tack: good tack
Phase separation: none
Surface properties: dry
Scent: initial—very clear after 24 hours—very clear after 17 months of storage initial—very clear, some loss of fragrance

EXAMPLE XX

The essence of oil of Citronellal was added at 0.5 weight percent to PSA. A master batch was prepared by the following formulations:

| Grams | Formulation |
|---|---|
| 50.00 | PSA |
| 0.045 | Citronellal |

This batch was hand-coated with a Meyer rod onto SCOTCHPAK ®1022 release liner, allowed to dry, and transfer-coated onto white kraft paper.

Following fabrication, the properties were evaluated with the following results:
Adhesion: good adhesive properties
Tack: good tack
Phase separation: none
Surface properties: dry
Scent: initial—very clear after 24 hours—very clear after 17 months of storage initial—very clear, some loss of fragrance

EXAMPLE XXI

The essence of oil of JOY ® was added at 1.0 weight percent to PSA. A master batch was prepared by the following formulations:

| Grams | Formulation |
|---|---|
| 50.00 | PSA |
| 0.09 | JOY ® |

This batch was hand-coated with a Meyer rod onto SCOTCHPAK ® 1022 release liner, allowed to dry, and transfer-coated onto white kraft paper.

Following fabrication, the properties were evaluated with the following results:
Adhesion: good adhesive properties
Tack: good tack
Surface properties: dry
Scent: initial—very clear after 24 hours—very clear after 17 months of storage initial—very clear, some loss of fragrance

EXAMPLE XXII

The essence of oil of YSL PARIS ® was added at 5.0 weight percent to PSA. A master batch was prepared by the following formulations:

| Grams | Formulation |
|---|---|
| 50.00 | PSA |
| 0.45 | YSL PARIS ® |

This batch was hand-coated with a Meyer rod onto SCOTCHPAK ® 1022 release liner, allowed to dry, and transfer-coated onto white kraft paper.

Following fabrication, the properties were evaluated with the following results:
Adhesion: good adhesive properties
Tack: good tack
Phase separation: none
Scent: initial—very clear after 24 hours—very clear after 17 months of storage initial—very clear, some loss of fragrance

EXAMPLE XXIII

The essence of oil of IVOIRE de BALMAIN TM was added at 5.0 weight percent to PSA. A master batch was prepared by the following formulations:

| Grams | Formulation |
|---|---|
| 50.00 | PSA |
| 0.45 | IVOIRE de BALMAIN TM |

This batch was hand-coated with a Meyer rod onto SCOTCHPAK ® 1022 release liner, allowed to dry, and transfer-coated onto white kraft paper.

Following fabrication, the properties were evaluated with the following results:
Adhesion: good adhesive properties
Tack: good tack
Phase separation: none
Surface properties: dry
Scent: initial—very clear after 24 hours—very clear after 17 months of storage initial—very clear, some loss of fragrance

EXAMPLE XXIV

The essence of oil of OSCAR de la RENTA ® was added at 1.0 weight percent to PSA. A master batch was prepared by the following formulations:

| Grams | Formulation |
|---|---|
| 50.00 | PSA |
| 0.09 | OSCAR de la RENTA ® |

This batch was hand-coated with a Meyer rod onto SCOTCHPAK ® 1022 release liner, allowed to dry, and transfer-coated onto white kraft paper.

Following fabrication, the properties were evaluated with the following results:
Adhesion: good adhesive properties
Tack: good tack
Phase separation: none
Surface properties: dry
Scent: initial—very clear after 24 hours—very clear after 17 months of storage initial—very clear, some loss of fragrance

EXAMPLE XXV

The essence of oil of Citronellal was added at 1.0 weight percent to RTV. A master batch of 18.0 grams was prepared by the following formulations:

| Grams | Formulation |
|---|---|
| 17.73 | RTV Base |
| 0.089 | RTV Catalyst |
| 0.18 | Citronellal |

This batch was compression molded between two sheets of Mylar ® in a 6″×6″×0.020″ mold at 100° C. for 15 minutes under 12 tons of pressure in a carver hydraulic press.

When curing was completed, the properties were analyzed with the following results:
Curing ability: good, cures completely
Elasticity: elastic (very little or no tear)
Phase separation: none
Surface properties: dry
Scent: initial—very clear after 24 hours—very clear

EXAMPLE XXVI

The essence of oil of Citronellal was added at 5.0 weight percent to RTV. A master batch of 18.0 grams was prepared by the following formulations:

| Grams | Formulation |
|---|---|
| 16.24 | RTV Base |
| 0.86 | RTV Catalyst |
| 0.90 | Citronellal |

This batch was compression molded between two sheets of Mylar ® in a 6″×6″×0.020″ mold at 80° C. for 15 minutes under 12 tons of pressure in a hydraulic press.

When curing was completed, the properties were analyzed with the following results:
Curing ability: good, complete cure
Elasticity: elastic (very little or no tear)
Phase separation: none
Surface properties: dry
Scent: initial—very clear after 24 hours—very clear

EXAMPLE XXVII

The essence of oil of Cineole was added at 1.0 weight percent to RTV. A master batch of 18.0 grams was prepared by the following formulations;

| Grams | Formulation |
|---|---|
| 17.73 | RTV Base |
| 0.089 | RTV Catalyst |

| Grams | Formulation |
|---|---|
| 0.18 | Cineole |

This batch was film-casted between two sheets of Mylar ® and oven-cured approximately one hour at 50° C..

When curing was completed, the properties were analyzed with the following results:
Curing ability: good, complete cure
Elasticity: elastic (very little or no tear)
Phase separation: none
Surface properties: dry
Scent: initial—very clear after 24 hours—very clear

EXAMPLE XXVIII

The essence of oil of Cineole was added at 5.0 weight percent to RTV. A master batch of 18.0 grams was prepared by the following formulations:

| Grams | Formulation |
|---|---|
| 16.24 | RTV Base |
| 0.86 | RTV Catalyst |
| 0.90 | Cineole |

This batch was film-casted between two sheets of Mylar ® and oven-cured approximately one hour at 50° C.

When curing was completed, the properties were analyzed with the following results:
Curing ability; good, complete cure
Elasticity: elastic (very little or no tear)
Phase separation: none
Surface properties: dry
Scent: initial—very clear after 24 hours—very clear

EXAMPLE XXIX

The essence of oil of Cineole was added at 1.0 weight percent to LTV. A master batch of 18.0 grams was prepared by the following formulations:

| Grams | Formulation |
|---|---|
| 16.04 | LTV Base |
| 1.78 | LTV Curing Agent |
| 0.18 | Cineole |

This batch was compression molded between two sheets of Mylar ® in a 6"×6"×0.020" mold at 80° C. for 15 minutes under 12 tons of pressure in a hydraulic press.

When curing was completed, the properties were analyzed with the following results:
Curing ability: good, complete cure
Elasticity: elastic (very little or no tear)
Phase separation: dry
Scent: initial—very clear after 24 hours—very clear

EXAMPLE XXX

The essence of oil of Citronellal was added at 5.0 weight percent to LTV. A master batch of 18.0 grams was prepared by the following formulations:

| Grams | Formulation |
|---|---|
| 15.39 | LTV Base |
| 1.71 | LTV Curing Agent |
| 0.90 | Citronellal |

This batch was compression molded between two sheets of Mylar ® in a 6"×6"×0.020" mold at 100° C. for 15 minutes under 12 tons of pressure in a carver hydraulic press.

When curing was completed, the properties were analyzed with the following results:
Curing ability: good, complete cure
Elasticity: elastic (very little or no tear)
Phase separation: none
Surface properties: dry
Scent: initial—very clear after 24 hours—very clear

EXAMPLE XXXI

The essence of oil of Cineole was added at 5.0 weight percent to LTV. A master batch of 18.0 grams was prepared by the following formulations:

| Grams | Formulation |
|---|---|
| 15.39 | LTV Base |
| 1.71 | LTV Curing Agent |
| 0.90 | Cineole |

This batch was compression molded between two sheets of Mylar ® in a 6"×6"×0.020" mold at 80° C. for 15 minutes under 12 tons of pressure in a hydraulic press.

When curing was completed, the properties were analyzed with the following resulting:
Curing ability: good, complete cure
Elasticity: elastic (very little or no tear)
Phase separation: none
Surface properties: dry
Scent: initial—very clear after 24 hours—very clear Following cure of the elastomer fragrance matrix, the polyester was removed from one surface of the matrix which was then transfer-coated with a 2 mil thick film of PSA-AC on SCOTCHPAK ® 1022 Release Liner. The laminates were die cut into 1 to 3 cm diameter discs for evaluations. The fragrance devices and formulations are set forth in Table IV.

TABLE IV
FORMULATIONS OF FRAGRANCE PATCH DEVICES

| Sample | Polymer | Method | Fragrance | Wt % Loading |
|---|---|---|---|---|
| 9 | LTV | molded | Citronellal | 0.5 |
| 10 | LTV | molded | Cineole | 1.0 |
| 11 | LTV | molded | IVOIRE de BALMAIN ™ (Chlon 18th Edition) | 1.0 |
| 12 | LTV | molded | OSCAR de la RENTA ® (Chlon 9th Edition) | 5.0 |
| 13 | LTV | molded | JOY ® (Chlon 5th Edition) | 5.0 |
| 14 | LTV | molded | Citronellal | 0.5 |
| 15 | LTV | molded | JOY ® (Chlon 5th Edition) | 1.0 |
| 16 | LTV | molded | Cineole | 0.5 |
| 17 | LTV | molded | YSL PARIS ® (Chlon 20th Edition) | 1.0 |
| 18 | LTV | molded | Cineole | 0.5 |
| 19 | PSA | cast | Cineole | 0.5 |
| 20 | PSA | cast | Citronellal | 0.5 |
| 21 | PSA | cast | JOY ® (Chlon 5th Edition) | 1.0 |

TABLE IV-continued

FORMULATIONS OF FRAGRANCE PATCH DEVICES

| Sample | Polymer | Method | Fragrance | Wt % Loading |
|---|---|---|---|---|
| 22 | PSA | cast | YSL PARIS ® (Chlon 20th Edition) | 5.0 |
| 23 | PSA | cast | IVOIRE de BALMAIN ™ (Chlon 18th Edition) | 5.0 |
| 24 | PSA | cast | OSCAR de la RENTA ® (Chlon 9th Edition) | 1.0 |
| 25 | RTV | molded | Citronellal | 1.0 |
| 26 | RTV | molded | Citronellal | 5.0 |
| 27 | RTV | cast | Cineole | 1.0 |
| 28 | RTV | cast | Cineole | 5.0 |
| 29 | LTV | molded | Cineole | 1.0 |
| 30 | LTV | molded | Citronellal | 5.0 |
| 31 | LTV | molded | Cineole | 5.0 |

Typical of the devices prepared in accordance with the present invention is an elastomer matrix fragrance device of four stacked layers. The top layer is, for example, an impermeable backing of Mylar ® about 5 mils in thickness which is removed from the device upon activation. The second layer is the elastomer-fragrance matrix and the matrix is approximately 20 mils in thickness. Layer three is of the material PSA-AC; this layer averages about 2 mils in thickness. The fourth layer is SCOTCHPAK ® 1022 release liner of 2 mils thickness which is removed prior to activation of the device. A second embodiment is an adhesive fragrance matrix device again of four stacked layers. The first layer is impermeable Mylar ® of 5 mils thickness which is removed upon activation of the device. The second layer is of kraft paper with a thickness of 5 mils. The third layer is PSA-fragrance matrix 2 mils in thickness. The fourth layer is SCOTCHPAK ® 1022 release liner, 2 mils in thickness, which is removed from the device prior to activation.

The rate and extent of cure, elasticity, phase separation of the fragrance oil from the cured elastomer, surface properties of the cured matrix, and organoleptic properties were evaluated in accordance with the following standards. Cure was rated on a scale of 1 to 3, where: 1=complete fast cure, 2=slow cure, and 3=no cure. Elasticity of the cured elastomer fragrance matrix was evaluated by pulling gently on the matrix and rated on a scale of 1 to 3 where: 1=elastic, no tear, 2=moderate tear, and 3=tears easily. Phase separation of the fragrance oil from the cured elastomer was rated as present (yes) or absent (no), and the degree of fragrance oil on the surface of the cured elastomer matrix was rated on a scale of 1 to 3 where: 1=oily, 2=slightly oily, and 3=dry.

The organoleptic scent characteristics of the fragrance devices were evaluated initially after fabrication by removing the release liner and Mylar ® protective backing, and adhering the system to a substrate. The degree of scent was noted at a distance of 5 feet from the device initially and after one week. Scent was rated on a scale of from 1 to 3 where: 1=very clear or the same as the initial scent, 2=slight decrease, and 3=marked decrease. Some devices stored for 17 months at room temperature were removed from polyethylene plastic storage bags and applied to wood and metal substrates and evaluated for initial degree of scent.

The properties of the fragrance adhesive patch devices are shown in Table V. After 17 months of storage, the release liner was easily removed and the systems adhered to both wood and metal substrates and liberated fragrance which was detectable up to 5 feet away.

All of the silicone rubber fragrance formulations cured into elastomeric matrices liberated fragrance oil, the scent of which could be detected up to 5 feet away. The cured properties of these formulations are shown in Table VI. All of the matrices were elastomeric with high tear strength, possessed a dry surface with no oiling or phase separation, and liberated scent for up to one week.

These fragrance devices were stored in polyethylene bags for 17 months at room temperature. They were removed from the bags, and the Mylar ® and release liner were removed from the devices which were applied to wood and metal substrates, and the degree of adhesion and presence of fragrance evaluated as shown in Table V. All of the devices adhered to both wood and metal surfaces and liberated fragrance detectable at a distance of 5 feet.

TABLE V

PROPERTIES OF FRAGRANCE ADHESIVE PATCH DEVICES

| Sample | Adhesion[a] | Tack[b] | Phase Separation | Surface[c] Properties | Scent[d] 24 hr | 1 wk | 17 mth[e] |
|---|---|---|---|---|---|---|---|
| 19 | 1 | 1 | no | 3 | 1 | 1 | 2 |
| 20 | 1 | 1 | no | 3 | 1 | 1 | 2 |
| 21 | 1 | 1 | no | 3 | 1 | 1 | 2 |
| 22 | 1 | 1 | no | 3 | 1 | 1 | 2 |
| 23 | 1 | 1 | no | 3 | 1 | 1 | 2 |
| 24 | 1 | 1 | no | 3 | 1 | 1 | 2 |

[a]Adhesion: 1 = good, high; 2 = moderate; 3 = poor, low
[b]Tack: 1 = good, high; 2 = moderate; 3 = poor, low
[c]Surface Properties: 1 = oily; 2 = slightly oily; 3 = dry
[d]Scent: 1 = very clear (same as initial); 2 = slight decrease; 3 = marked decrease
[e]Samples stored in polyethylene bags for 17 months at room temperature were removed and evaluated for initial organoleptic properties.

TABLE VI

CURED PROPERTIES OF FRAGRANCE ELASTOMER PATCH DEVICES

| Sample | Cure[a] | Elasticity[b] | Phase[c] Separation | Surface[d] Properties | Scent[e] 24 hr | 1 wk | 17 mth[f] |
|---|---|---|---|---|---|---|---|
| 9 | 1 | 1 | no | 3 | 1 | 1 | 2 |
| 10 | 1 | 1 | no | 3 | 1 | 1 | 2 |
| 11 | 1 | 1 | no | 3 | 1 | 1 | 2 |
| 12 | 1 | 1 | no | 3 | 1 | 1 | 2 |
| 13 | 1 | 1 | no | 3 | 1 | 1 | 2 |
| 14 | 1 | 1 | no | 3 | 1 | 1 | 2 |
| 15 | 1 | 1 | no | 3 | 1 | 1 | 2 |
| 16 | 1 | 1 | no | 3 | 1 | 1 | 2 |
| 17 | 1 | 1 | no | 3 | 1 | 1 | 2 |
| 18 | 1 | 1 | no | 3 | 1 | 1 | 2 |
| 19 | 1 | 1 | no | 3 | 1 | 1 | 2 |
| 20 | 1 | 1 | no | 3 | 1 | 1 | 2 |
| 25 | 1 | 1 | no | 3 | 1 | 1 | 2 |
| 26 | 1 | 1 | no | 3 | 1 | 1 | 2 |
| 27 | 1 | 1 | no | 3 | 1 | 1 | 2 |
| 28 | 1 | 1 | no | 3 | 1 | 1 | 2 |
| 29 | 1 | 1 | no | 3 | 1 | 1 | 2 |
| 30 | 1 | 1 | no | 3 | 1 | 1 | 2 |
| 31 | 1 | 1 | no | 3 | 1 | 1 | 2 |

[a]Cure: 1 = fast cure; 2 = slow cure; 3 = no cure
[b]Elasticity: 1 = elastic, no tear; 2 = moderate tear; 3 = easy tear
[c]Phase Separation: yes; no
[d]Surface Properties: 1 = oily; 2 = slightly oily; 3 = dry
[e]Scent: 1 = very clear (same as initial); 2 = slight decrease; 3 = marked decrease
[f]Samples stored in polyethylene bags for 17 months at room temperature were removed and evaluated for initial organoleptic properties.

The foregoing demonstrates that several different types of fragrance oils can be incorporated into a two-part tin catalyzed room temperature condensation cure liquid silicone rubber to form an elastomeric fragrance matrix. These fragrances can also be incorporated into a two-part elevated temperature addition cure liquid silicone rubber including LTV elastomers to form elastomer matrices which exhibit controlled release of fragrances for up to about one week. The devices can be fabricated by either molding or film cast processes between various substrates. A silicone pressure sensitive adhesive is applied to the device to form a multi-laminate system. Fragrance oils can also be incorporated into pressure sensitive adhesives which function as the matrix for the device for the controlled release of fragrance.

These devices may be applied to various substrates including wood, metal or skin to liberate fragrance over a prolonged period of time, and have industrial, personal and household applications as air fresheners and controlled release perfumes as noted above.

It will be apparent from the foregoing that many other variations and modifications may be made in the structures, compounds, compositions, and methods described herein without departing substantially from the essential concepts of the present invention. Accordingly, it should be clearly understood that the forms of the invention described herein and depicted in the accompanying drawings are exemplary only and are not intended as limitations on the scope of the present invention.

That which is claimed is:

1. A multi-layered multi-laminate sustained release device capable of releasing fragrances at a controlled rate for a prolonged period of time comprising a first layer of a pressure sensitive adhesive release liner for providing a protective peel strip for the device, a second layer of a silicone pressure sensitive adhesive for adhering the device to a substrate to which it is applied, a third layer of a fragrance impregnated matrix which is a silicone material selected from the group consisting of silicone elastomers, silicone elastomers having adhesive characteristics, and elastomeric silicone pressure sensitive adhesives, a fourth layer of a permeable facestock backing member on the surface of the device for controlling the rate of release of the fragrance from the impregnated matrix, the fragrance in the impregnated matrix constituting of from about one-half of one percent to about forty percent by weight of the impregnated matrix, the matrix including a release rate modifying excipient for increasing the solubility of the fragrance in the matrix resulting in an increase in the release capability of the device.

2. The device in claim 1 wherein the excipient is a material selected from the group consisting of glycerol, propylene glycol, polyethylene glycol, mineral oil, coconut oil, isopropyl palmitate, and isopropyl myristate.

3. The device in claim 2 wherein the pressure sensitive adhesive release liner is a polyester substrate.

4. The device in claim 3 wherein the pressure sensitive adhesive release liner contains a silicone pressure sensitive adhesive release coating.

5. The device in claim 1 wherein the permeable facestock backing member is constructed of a material selected from the group consisting of wovens, non-wovens, and porous thermoplastics, and includes decorative, ornate, and varied colored, designs on the surface thereof.

6. The device in claim 1 wherein the fragrance impregnated matrix constitutes at least three separate and distinct layers, each of the three layers of the fragrance impregnated matrix including a fragrance differing from the fragrance in each of the other of the layers of the matrix.

7. A multi-layered multi-laminate sustained release device capable of releasing fragrances at a controlled rate for a prolonged period of time comprising a first layer of a pressure and sensitive adhesive release liner for providing a protective peel strip for the device, a second layer of a silicone pressure sensitive adhesive for adhering the device to a substrate to which it is applied, a third layer of a fragrance impregnated matrix which is a silicone material selected from the group consisting of silicone elastomers, silicone elastomers having adhesive characteristics, and elastomeric silicone pressure sensitive adhesives, a fourth layer of a permeable facestock backing member on the surface of the device for controlling the rate of release of the fragrance from the impregnated matrix, the device including therein at least one impermeable backing member for preventing the fragrance of the impregnated matrix from interacting with the substrate to which it is applied, the fragrance in the impregnated matrix constituting of from about one-half of one percent to about forty percent by weight of the impregnated matrix, the matrix including a release rate modifying excipient for increasing the solubility of the fragrance in the matrix resulting in an increase in the release capability of the device.

8. The device in claim 7 wherein the excipient is a material selected from the group consisting of glycerol, propylene glycol, polyethylene glycol, mineral oil, coconut oil, isopropyl palmitate, and isopropyl myristate.

9. The device in claim 8 wherein the pressure and sensitive adhesive release liner is a polyester substrate.

10. The device in claim 8 wherein the pressure sensitive adhesive release liner includes a material selected from the group consisting of silicone acrylic and rubber-based pressure sensitive adhesive release coatings.

11. The device in claim 7 wherein the permeable facestock backing member is constructed of a material selected from the group consisting of wovens, nonwovens, and porous thermoplastics, and includes decorative, ornate, and varied colored, designs on the surface thereof.

12. The device in claim 7 wherein the fragrance impregnated matrix constitutes at least three separate and distinct layers, each of the three layers of the fragrance impregnated matrix including a fragrance differing from the fragrance in one of the other of the layers of the matrix.

13. The device as claimed in claim 7 wherein the silicone material is selected from the group consisting of silicone pressure sensitive adhesives, platinum addition cured silicone elastomers, tin catalyzed condensation cured silicone elastomers, photoinitiated UV cured silicone elastomers, acetoxy cured silicone elastomers, methoxy cured silicone elastomers, and oxime cured silicone elastomers.

14. The device in claim 13 wherein the silicone material is a tin catalyzed condensation cured silicone elastomer and the catalyst is stannous octoate.

15. The device in claim 14 wherein there is included at least one other layer of a silicone pressure sensitive adhesive in addition to said second layer of silicone pressure sensitive adhesive.

16. The device in claim 14 wherein there is included at least two other layers of a silicone pressure sensitive adhesive in addition to said second layer of silicone pressure sensitive adhesive.

17. A multi-layered multi-laminate sustained release device capable of releasing fragrances at a controlled rate for a prolonged period of time comprising a first layer of a pressure and sensitive adhesive release liner for providing a protective peel strip for the device, a second layer of a silicone pressure sensitive adhesive for adhering the device to a substrate to which it is applied, a third layer of a fragrance impregnated matrix which is a silicone material selected from the group consisting of tin catalyzed room temperature condensation cured liquid silicone rubbers, elevated temperature addition cured liquid silicone rubbers and silicone pressure sensitive adhesives, a fourth layer of a permeable facestock backing member on the surface of the device for controlling the rate of release of the fragrance from the impregnated matrix, the fragrance in the impregnated matrix constituting of from about one-half of one percent to about forty percent by weight of the impregnated matrix, the matrix including a release rate modifying excipient for increasing the solubility of the fragrance in the matrix resulting in an increase in the release capability of the device.

18. The device in claim 17 wherein the excipient is a material selected from the group consisting of glycerol, propylene glycol, polyethylene glycol, mineral oil, coconut oil, isopropyl palmitate, and isopropyl myristate.

19. The device in claim 19 wherein the pressure and sensitive adhesive release liner is a polyester material.

20. The device in claim 18 wherein the pressure and sensitive adhesive release liner contains a silicone pressure sensitive adhesive release coating.

21. The device in claim 17 wherein the permeable facestock backing member is constructed of a material selected from the group consisting of wovens, nonwovens, and porous thermoplastics, and includes decorative, ornate, and varied colored, designs on the surface thereof.

22. The device in claim 17 wherein the fragrance impregnated matrix constitutes at least three separate and distinct layers, each of the three layers of the fragrance impregnated matrix including a fragrance differing from the fragrance in each one of the other of the layers of the matrix.

* * * * *